United States Patent [19]

Ohashi et al.

[11] 4,246,428

[45] Jan. 20, 1981

[54] METHOD FOR SEPARATION OF DIASTEREOISOMERIC 3-(3,4-DIBENZYLOXYPHENYL)SERINE

[75] Inventors: Naohito Ohashi; Yoshinori Takashima, both of Nishinomiya; Junki Katsube, Toyonaka, all of Japan

[73] Assignee: Sumitomo Chemical Company, Limited, Osaka, Japan

[21] Appl. No.: 922,665

[22] Filed: Jul. 7, 1978

[30] Foreign Application Priority Data

Jul. 11, 1977 [JP] Japan .................................. 52-83128

[51] Int. Cl.$^3$ .............................................. C07C 51/43
[52] U.S. Cl. .................................... 562/401; 562/402
[58] Field of Search ................... 562/401, 402; 560/39

[56] References Cited

U.S. PATENT DOCUMENTS

| | | | |
|---|---|---|---|
| 3,182,079 | 5/1965 | Talsumi et al. | 562/402 |
| 3,723,514 | 3/1973 | Hegedus et al. | 562/402 |
| 3,830,836 | 8/1974 | Soichiro et al. | 562/402 |

OTHER PUBLICATIONS

Bolhofer, J.A.C.S., vol. 76, pp. 1322–1326 (1954).

*Primary Examiner*—James H. Reamer
*Attorney, Agent, or Firm*—Birch, Stewart, Kolasch & Birch

[57] ABSTRACT

A method for separation of diastereoisomeric 3-(3,4-dibenzyloxyphenyl)serine, which comprises reacting a mixture of the threo isomer and erythro isomer of 3-(3,4-dibenzyloxyphenyl)serine with a mineral acid and separating the mixture of the resulting mineral acid salts of the threo isomer and erythro isomer into each mineral acid salt by a conventional fractional crystallization utilizing the difference in solubility of the mineral acid salts, and optionally converting the separated mineral acid salt into a free isomer. Said 3-(3,4-dibenzyloxyphenyl)serine or a mineral acid salt thereof thus separated can give 3-(3,4-dihydroxyphenyl)serine which is a precursor of norepinephrine and which has activity in the circulatory system or psychotropic activities by removing the benzyl group therefrom.

4 Claims, No Drawings

METHOD FOR SEPARATION OF DIASTEREOISOMERIC 3-(3,4-DIBENZYLOXYPHENYL)SERINE

The present invention relates to an improved method for separation of diastereoisomeric 3-(3,4-dibenzyloxyphenyl)serine. More particularly, it relates to a method for separation of threo- and erythro-3-(3,4-dibenzyloxyphenyl)serine by reacting the diastereoisomers with a mineral acid and separating the mineral acid salts of the diastereoisomers utilizing the difference of the solubility of the mineral acid salts and optionally converting each mineral acid salt into each free isomer by treatment with a base.

It is known that threo- or erythro-3-(3,4-dibenzyloxyphenyl)serine or a mineral acid salt thereof can give the corresponding threo- or erythro-3-(3,4-dihydroxyphenyl)serine (hereinafter, referred to as "DOPS") or a mineral acid salt thereof, respectively, by debenzylation thereof. It is also known that the threo- or erythro-DOPS is a precursor of norepinephrine which is an important catecholamine in vivo, and which also shows activity in the circulatory system or psychotropic activities. (cf. Japanese Patent Laid Open Publication (unexamined) No. 49,252/1975).

DOPS is usually prepared by condensing 3,4-dibenzyloxybenzaldehyde and glycine and then subjecting the resulting 3-(3,4-dibenzyloxyphenyl)serine to debenzylation as mentioned above. However, according to such a synthetic process, the desired DOPS is obtained in a mixture of diastereoisomers (i.e. the threo isomer and erythro isomer), and hence, the mixture should be separated into each isomer at any stage of the process.

The separation of the diastereoisomers has hitherto been carried out by the following methods:

(1) Fractional crystallization of threo- and erythro-3-(3,4-dibenzyloxyphenyl)serine [cf. J. Am. Chem. Soc., Vol. 76, page 1322 (1954)]

(2) Separation in the form of the dicyclohexylamine salt of threo- and erythro-3-(3,4-dibenzyloxyphenyl)-N-carbobenzoxyserine (cf. Japanese Patent Laid Open Publication (unexamined) No. 49,252/1975).

However, the above method (1) has defects in its reproducibility and in the operation on an industrial scale, and the method (2) is not suitable from an economical viewpoint.

As a result of the present inventors' intensive study, there has been found an economical and industrial method for separation of diastereoisomeric 3-(3,4-dibenzyloxyphenyl)serine into each threo isomer and erythro isomer in the form of a mineral acid salt thereof. The present inventors have found that although erythro-3-(3,4-dibenzyloxyphenyl)serine is more difficultly soluble than the threo isomer thereof, when they are converted into a mineral acid salt thereof, the solubility reverses, that is, the mineral acid salt of the threo isomer is more difficultly soluble than the mineral acid salt of the erythro isomer, and further, the difference of the solubility thereof becomes remarkably larger, and hence, by utilizing this difference of solubility, both isomers can easily be separated into each of the respective isomers.

An object of the present invention is to provide an improved method for separation of diastereoisomeric 3-(3,4-dibenzyloxyphenyl)serine. Another object of the invention is to provide a method for preparing pure threo- or erythro-DOPS. These and other objects of the invention will be apparent from the following description.

According to the present invention, the mixture of the diastereoisomeric 3-(3,4-dibenzyloxyphenyl)serine is reacted with a mineral acid, and the mixture of the resulting mineral acid salts of the threo isomer and erythro isomer is isolated from the reaction mixture and then is separated into each mineral acid salt of the isomers by fractional crystallization utilizing the difference of solubility thereof. As a result, the more difficultly soluble mineral acid salt of the threo isomer is obtained in a crystalline form and the mineral acid salt of the erythro isomer is obtained from the solution after separation of the crystals of the mineral acid salt of the threo isomer.

Alternatively, the mixture of mineral acid salts of the isomers may be subjected to separation into each isomer without isolation from the reaction mixture. That is, threo- and erythro-3-(3,4-dibenzyloxyphenyl)serine are reacted with a mineral acid in a suitable solvent, and thereby, the resulting mineral acid salt of the threo isomer which is more difficultly soluble in the solvent can be obtained in the form of a crystalline material without isolating the mineral acid salts from the reaction mixture. Optionally, the mineral acid salt of the erythro isomer is obtained from the remaining solution. The thus separated mineral acid salt of the threo isomer or erythro isomer then may optionally be converted into free threo- or erythro-3-(3,4-dibenzyloxyphenyl)serine.

The threo- or erythro-3-(3,4-dibenzyloxyphenyl)serine or a mineral acid salt thereof obtained by the above method can be subjected to a debenzylation reaction to give threo- or erythro-DOPS, respectively.

The details of the method of the present invention are as follows.

In the case where the mixture of the mineral acid salts of threo- and erythro-3-(3,4-dibenzyloxyphenyl)serine is subjected to fractional crystallization after isolating the mixture from the reaction mixture, the threo- and erythro-3-(3,4-dibenzyloxyphenyl)serine are reacted with one mol or more, preferably one to two mols, of a mineral acid per one mol of the threo and erythro isomers in an appropriate solvent, such as water, methanol, ethanol, acetone, N,N-dimethylformamide, or a mixture thereof, at room temperature or an elevated temperature, preferably at 20° to 60° C. The mixture of the resulting mineral acid salts of the threo and erythro isomers can be isolated from the reaction mixture by evaporating the solvent therefrom under reduced pressure or by adding a solvent, in which the mineral acid salts are hardly or only slightly soluble, such as diethyl ether, toluene or n-hexane. In this method, the starting threo- and erythro-3-(3,4-dibenzyloxyphenyl)serine may have any molar ratio of the threo isomer and erythro isomer. Mineral acids used in the present invention include hydrochloric acid, hydrobromic acid, hydroiodic acid and nitric acid. The preferred mineral acid is hydrochloric acid from the viewpoints of the price and ease in handling thereof.

The mixture of the mineral acid salts of the threo isomer and erythro isomer thus isolated is then subjected to fractional crystallization by a conventional method to give a comparatively hardly soluble mineral acid salt of threo-3-(3,4-dibenzyloxyphenyl)serine. The fractional crystallization of the present invention can generally be carried out by dissolving the mixture in a solvent which is heated at a temperature a little higher than that sufficient for dissolving it, and subsequently gradually cooling the solution to room temperature or lower, preferably 30° to −20° C., to crystallize out the mineral acid salt of the threo isomer, while the mineral acid salt of the erythro isomer is dissolved in the solution. Solvents useful for the fractional crystallization are not necessarily specified, unless the mineral acid salts are decomposed or hydrolyzed thereby. However, it is not preferable to use a solvent which can not or can only slightly dissolve the mineral acid salts, such as diethyl ether, toluene, or a solvent containing a large amount of diethyl ether or toluene. Suitable examples of the solvent useful for the fractional crystallization are water, ethanol, isopropanol, acetone, ethyl acetate, and mixtures thereof.

After separating crystals of the mineral acid salt of the threo isomer, the mineral acid salt of erythro-3-(3,4-dibenzyloxyphenyl)serine may be obtained in the form of a crystalline material from the remaining solution by adding a solvent which can hardly or only slightly dissolve the mineral acid salt of the erythro isomer (e.g. diethyl ether, toluene), or by concentrating the solution under reduced pressure, or by replacing the solvent of the solution by another solvent which can hardly or only slightly dissolve the mineral acid salt of the erythro isomer.

In the case where the mixture of mineral acid salts of threo- and erythro-3-(3,4-dibenzyloxyphenyl)serine is separated into each mineral acid salt of the threo isomer and the erythro isomer without isolating the mixture from the reaction mixture, threo- and erythro-3-(3,4-dibenzyloxyphenyl)serine is reacted with one mol or more of a mineral acid per one mol of the threo and erythro isomers in an appropriate solvent at room temperature or an elevated temperature in a similar manner as in the above case of separation after isolating the mixture of the mineral acid salts from the reaction mixture. Although the reaction and subsequent separation may be carried out at room temperature or an elevated temperature, it is preferable to accelerate the reaction by heating during the first stage and subsequently gradually cooling. For instance, the reaction of the mixture of threo isomer and erythro isomer with a mineral acid is carried out at a temperature of 20° to 60° C., and thereafter, the reaction mixture is gradually cooled to room temperature or lower, preferably −20° to 30° C., by which the comparatively hardly soluble mineral acid salt of threo-3-(3,4-dibenzyloxyphenyl)serine is obtained in the form of a crystalline material. In this method, the starting threo- and erythro-3-(3,4-dibenzyloxyphenyl)serine may have any ratio of the threo isomer and erythro isomer. The mineral acid includes the same compounds as used in the above case of separation after isolation of the mixture of mineral acid salts from the reaction mixture. The preferred mineral acid is hydrochloric acid. The solvent used in this method includes the same solvent as used in the above fractional crystallization, i.e. water, ethanol, isopropanol, acetone, ethyl acetate, and mixtures thereof.

After separating crystals of the mineral acid salt of the threo isomer, the mineral acid salt of erythro-3-(3,4-dibenzyloxyphenyl)serine may be obtained in the form of a crystalline material from the remaining solution in the same manner as described in the above method of separation of the mineral acid salts after isolation of the mixture of mineral acid salts from the reaction mixture.

The thus separated mineral acid salt of threo- or erythro-3-(3,4-dibenzyloxyphenyl)serine is optionally converted into free threo-3-(3,4-dibenzyloxyphenyl)serine or erythro-3-(3,4-dibenzyloxyphenyl)serine by a conventional process, for instance, by treating the mineral acid salt with a base, such as sodium hydroxide, sodium acetate or diethylamine.

The present invention is illustrated by the following Examples, but is not limited thereto.

EXAMPLE 1

Threo- and erythro-3-(3,4-dibenzyloxyphenyl)serine (molar ratio of threo isomer: erythro isomer = about 3:1, 5 g) is dissolved in a mixture of methanol (30 ml) and 3N hydrochloric acid (10 ml), and the mixture is distilled under reduced pressure to remove the solvent, and thereby threo- and erythro-3-(3,4-dibenzyloxyphenyl)serine hydrochloride are obtained. The salts thus obtained are recrystallized from ethanol to give threo-3-(3,4-dibenzyloxyphenyl)serine hydrochloride (2.7 g), m.p. 150°–154° C.

The remaining solution is then distilled to remove the solvent, and thereto is added isopropanol, and thereby there are obtained crystals of erythro-3-(3,4-dibenzyloxyphenyl)serine hydrochloride (1.3 g), m.p. 136°–140° C.

EXAMPLE 2

To threo- and erythro-3-(3,4-dibenzyloxyphenyl)serine (molar ratio of threo isomer:erythro isomer = about 3:1, 92 g) are added ethanol (330 ml) and concentrated hydrochloric acid (35 ml), and the mixture is stirred at 40°–45° C. for 1 hour, at room temperature for 1.5 hour and further under ice-cooling for 2 hours. The precipitated crystals are collected by filtration to give threo-3-(3,4-dibenzyloxyphenyl)serine hydrochloride (61.5 g), m.p. 143°–145° C.

To the remaining solution is added diethyl ether, and the mixture is allowed to stand at room temperature overnight. The precipitated crystals are collected by filtration to give erythro-3-(3,4-dibenzyloxyphenyl)serine hydrochloride (7.8 g), m.p. 138°–142° C. After separating the salt, the solution is distilled to remove the solvent, and thereto is added acetone with heating, and the mixture is allowed to stand at room temperature. The precipitated crystals are collected by filtration to give erythro-3-(3,4-dibenzyloxyphenyl)serine hydrochloride (10.6 g), m.p. 139°–142.5° C. Total yield of the erythro isomer hydrochloride is 18.4 g.

EXAMPLE 3

To threo- and erythro-3-(3,4-dibenzyloxyphenyl)serine (molar ratio of threo isomer:erythro isomer = about 3:1, 1 g) are added isopropanol (15 ml) and concentrated hydrochloric acid (1.5 ml), and the mixture is stirred at 40°–45° C. for 1 hour, at room temperature for 30 minutes and further under ice-cooling for 2 hours. The precipitated crystals are collected by filtration to give the threo isomer hydrochloride (0.68 g), m.p. 145°–148° C. The remaining mixture is distilled to remove the solvent, and thereto is added acetone. The precipitated crystals are collected by filtration to give the erythro isomer hydrochloride (0.2 g), m.p. 128°–132° C.

EXAMPLE 4

To threo- and erythro-3-(3,4-dibenzyloxyphenyl)serine (molar ratio of the threo isomer:erythro isomer = about 3:1, 7 g) are added 95% ethanol (44 ml) and concentrated hydrochloric acid (4.4 ml), and the mixture is treated in the same manner as described in Example 3 to give the threo isomer hydrochloride (4.1 g), m.p. 149°–154° C. and the erythro isomer hydrochloride (1.7 g), m.p. 136°–139° C.

EXAMPLE 5

To threo- and erythro-3-(3,4-dibenzyloxyphenyl)serine (0.10 g) are added isopropanol (1 ml) and 48% hydrobromic acid (0.20 g) and the mixture is stirred at room temperature for 30 minutes and further under ice-cooling for 4 hours. The precipitated crystals are collected by filtration to give the threo isomer hydrobromide, m.p. 153°–154° C.

EXAMPLE 6

In the same manner as described in Example 5 except that 57% hydroiodic acid (0.2 g) is used as a mineral acid, the threo and erythro isomers are reacted. To the reaction mixture is added diethyl ether under ice-cooling, and the precipitated crystals are collected by filtration to give the threo isomer hydroiodide, m.p. 129°–132° C.

EXAMPLE 7

Example 5 is repeated except that 60% nitric acid (0.1 ml) is used as the mineral acid and there is obtained the threo isomer nitrate, m.p. 127°–128° C.

What is claimed is:

1. A method for the separation of diastereoisomeric 3-(3,4-dibenzyloxyphenyl)serine, which comprises the steps of; reacting a mixture of the threo isomer and the erythro isomer of 3-(3,4-dibenzyloxyphenyl)serine with a mineral acid selected from the group consisting of hydrochloric acid, hydrobromic acid, hydroiodic acid, and nitric acid, thereby forming the mineral acid salts of the threo and erythro isomers, respectively, and selectively crystallizing the threo isomer salt from a diastereoisomeric solution of the mineral acid salts in a solvent selected from the group consisting of water, ethanol, isopropanol, acetone, ethyl acetate and mixtures thereof.

2. A method according to claim 1, wherein the separation of the mixture of mineral acid salt of threo isomer and erythro isomer is carried out after isolating the mixture of the mineral acid salts from the reaction mixture and then subjecting the isolated mixture to fractional crystallization with said solvent.

3. A method according to claim 1, wherein the separation of the mixture of mineral acid salts is carried out directly from the reaction mixture utilizing the difference of solubility of the mineral acid salts in said solvent in the reaction system.

4. A method according to claim 1, wherein the separated mineral acid salt is converted into the free isomer thereof.

* * * * *